(12) United States Patent
Davey

(10) Patent No.: US 8,617,116 B2
(45) Date of Patent: Dec. 31, 2013

(54) DEFORMABLE MEDICAL IMPLANT

(75) Inventor: Christopher Davey, Galway (IE)

(73) Assignee: Marvao Medical Devices Ltd. (IE)

( * ) Notice: Subject to any disclaimer, the term of this patent is extended or adjusted under 35 U.S.C. 154(b) by 162 days.

(21) Appl. No.: 12/412,464

(22) Filed: Mar. 27, 2009

(65) Prior Publication Data
US 2010/0249712 A1  Sep. 30, 2010

(51) Int. Cl.
*A61M 5/32* (2006.01)

(52) U.S. Cl.
USPC ........................................ 604/175

(58) Field of Classification Search
USPC ............... 604/174–176, 288.01–288.04, 513, 604/891.1
See application file for complete search history.

(56) References Cited

U.S. PATENT DOCUMENTS

| | | |
|---|---|---|
| 3,663,965 A | 5/1972 | Lee et al. |
| 3,752,162 A | 8/1973 | Newash |
| 4,004,298 A | 1/1977 | Freed |
| 4,134,402 A | 1/1979 | Mahurkar |
| 4,266,999 A | 5/1981 | Baier |
| 4,327,722 A | 5/1982 | Groshong et al. |
| 4,405,305 A | 9/1983 | Stephen et al. |
| 4,488,877 A | 12/1984 | Klein et al. |
| 4,578,063 A | 3/1986 | Inman et al. |
| 4,583,968 A | 4/1986 | Mahurkar |
| 4,654,033 A | 3/1987 | Lapeyre et al. |
| 4,668,222 A | 5/1987 | Poirier |
| 4,673,394 A | 6/1987 | Fenton, Jr. et al. |
| 4,676,782 A | 6/1987 | Yamamoto et al. |
| 4,808,155 A | 2/1989 | Mahurkar |
| 4,886,502 A | 12/1989 | Poirier et al. |
| 4,897,081 A | 1/1990 | Poirier et al. |
| 4,898,669 A | 2/1990 | Tesio |
| 4,935,004 A | 6/1990 | Cruz |
| 4,959,054 A | 9/1990 | Heimke et al. |
| 5,084,024 A | 1/1992 | Skinner |
| 5,098,397 A | 3/1992 | Svensson et al. |
| 5,100,392 A | 3/1992 | Orth et al. |
| 5,156,597 A | 10/1992 | Verreet et al. |
| 5,171,216 A | 12/1992 | Dasse et al. |
| 5,242,415 A | 9/1993 | Kantrowitz et al. |
| 5,562,618 A | 10/1996 | Cai et al. |
| 5,624,392 A | 4/1997 | Saab |
| 5,662,616 A | 9/1997 | Bousquet |

(Continued)

OTHER PUBLICATIONS

Raad, et al., Arch Internal Medicine, "Intravascular Catheter-Related Infections: New Horizons and Recent Advances", vol. 162, pp. 871-878, Apr. 2002.

*Primary Examiner* — Kevin C Sirmons
*Assistant Examiner* — Imani Hayman
(74) *Attorney, Agent, or Firm* — Onello & Mello, LLP; David Silverstein

(57) ABSTRACT

The present invention comprises an implantable subcutaneous port for anchoring a transcutaneous treatment component. The implantable subcutaneous port comprises a body portion and one or more frangible lines formed within the body portion. The body portion is adapted for receiving the transcutaneous treatment component beneath the point of entry into the physiology of a patient and routing the transcutaneous treatment component. The body portion is produced from a deformable material and has an area footprint and defines a support wall through which the transcutaneous treatment component enters the body portion. Fracturing the one or more frangible lines formed within the body portion enables removal of the body portion from the physiology of a patient through a transcutaneous opening defining an area of less than thirty percent of the area footprint of the body portion.

41 Claims, 13 Drawing Sheets

(56) References Cited

U.S. PATENT DOCUMENTS

| | | |
|---|---|---|
| 5,685,878 A | 11/1997 | Falwell et al. |
| 5,718,678 A | 2/1998 | Fleming, III |
| 5,718,692 A | 2/1998 | Schon et al. |
| 5,743,873 A | 4/1998 | Cai et al. |
| 5,766,249 A | 6/1998 | Griffith |
| 5,776,111 A | 7/1998 | Tesio |
| 5,823,994 A | 10/1998 | Sharkey et al. |
| 5,830,184 A | 11/1998 | Basta |
| 5,848,987 A | 12/1998 | Baudino et al. |
| 5,882,341 A | 3/1999 | Bousquet |
| 5,902,268 A | 5/1999 | Saab |
| 5,947,953 A | 9/1999 | Ash et al. |
| 5,989,213 A | 11/1999 | Maginot |
| 6,033,382 A | 3/2000 | Basta |
| 6,050,979 A | 4/2000 | Haemmerle et al. |
| 6,099,508 A | 8/2000 | Bousquet |
| 6,117,163 A | 9/2000 | Bierman |
| 6,190,349 B1 | 2/2001 | Ash et al. |
| 6,238,369 B1 | 5/2001 | Burbank et al. |
| 6,264,673 B1 | 7/2001 | Egnelov et al. |
| 6,355,020 B1 | 3/2002 | Bousquet |
| 6,520,949 B2 | 2/2003 | St. Germain |
| 6,595,966 B2 | 7/2003 | Davey et al. |
| 6,605,063 B2 | 8/2003 | Bousquet |
| 6,638,242 B2 | 10/2003 | Wilson et al. |
| 6,682,519 B1 | 1/2004 | Schon |
| 6,695,832 B2 | 2/2004 | Schon et al. |
| 6,719,724 B1 | 4/2004 | Walker et al. |
| 6,719,749 B1 | 4/2004 | Schweikert et al. |
| 6,872,198 B1 | 3/2005 | Wilson et al. |
| 6,969,381 B2 | 11/2005 | Voorhees |
| 7,014,623 B2 | 3/2006 | Prestidge et al. |
| 7,018,374 B2 | 3/2006 | Schon et al. |
| 7,811,257 B2 | 10/2010 | Saab |
| 2003/0229323 A1 | 12/2003 | Haarala et al. |
| 2004/0181240 A1 | 9/2004 | Tseng et al. |
| 2004/0204687 A1* | 10/2004 | Mogensen et al. ............ 604/181 |
| 2004/0236314 A1 | 11/2004 | Saab |
| 2005/0107753 A1 | 5/2005 | Rezai et al. |
| 2005/0208095 A1 | 9/2005 | Hunter et al. |
| 2006/0241737 A1 | 10/2006 | Tockman et al. |
| 2007/0043323 A1 | 2/2007 | Davey |
| 2007/0066966 A1 | 3/2007 | Davey |
| 2007/0219510 A1 | 9/2007 | Zinn et al. |
| 2007/0225642 A1 | 9/2007 | Houser et al. |
| 2009/0131919 A1 | 5/2009 | Davey |

* cited by examiner

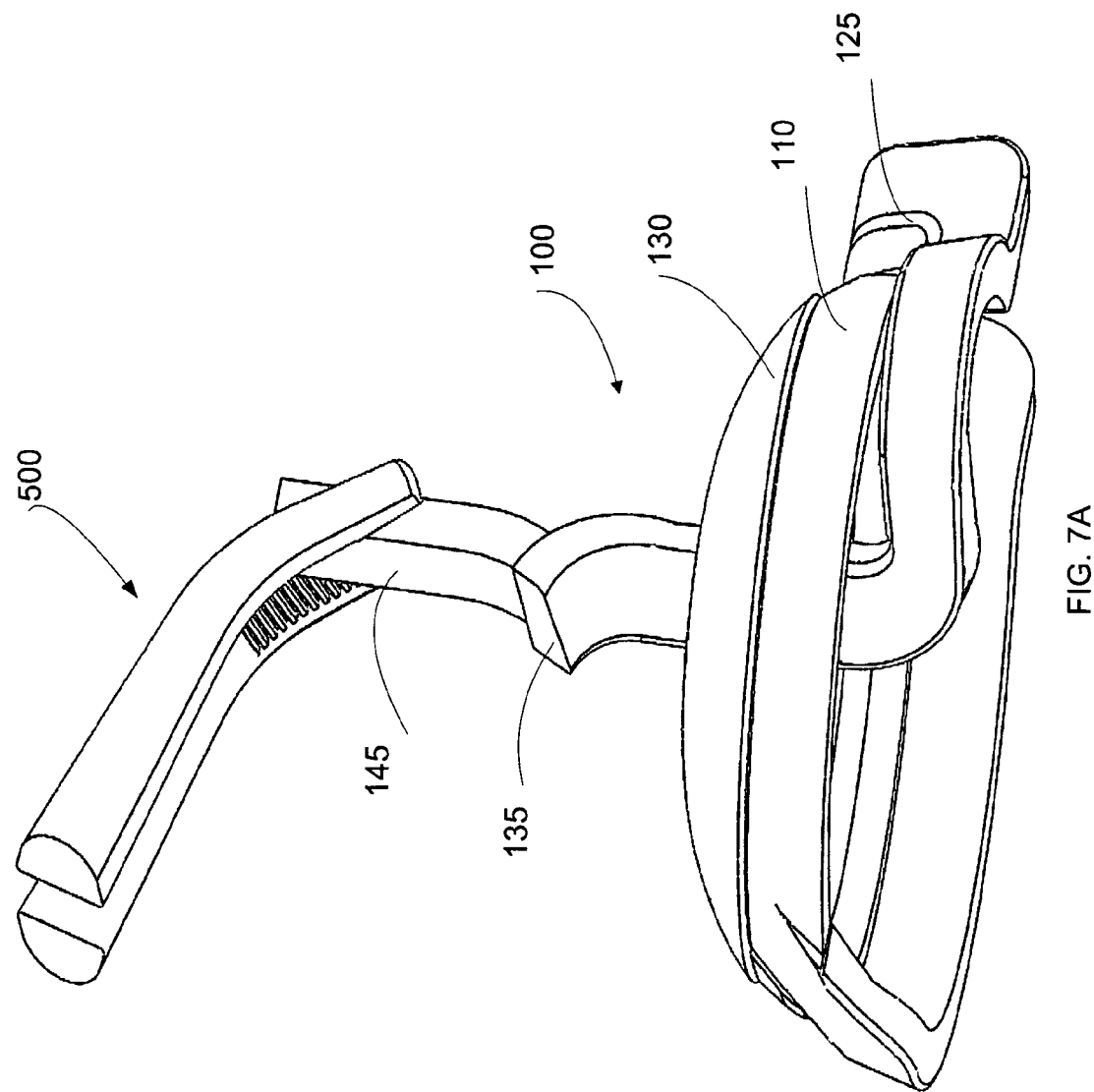

DEFORMABLE MEDICAL IMPLANT

BACKGROUND OF THE INVENTION

1. Field of the Invention

The present invention relates generally to the field of medical devices. In particular, the present invention relates to long term, implantable devices that permits access to inner physiology and that enable non-traumatic removal following treatment.

2. Summary of the Related Art

Medically treating a patient often requires long term placement of a medical device across one or more organ systems to establish access to a specifically targeted interior body site for diagnostic or therapeutic purposes. One common example is the establishment of percutaneous vascular access for purposes of administering liquid therapeutic agents, removing bodily fluids for testing or monitoring, treating bodily fluids before being returned to the body, and/or disposing of bodily fluids.

Particularly in the case of administering fluids to the body or removing fluids from the body continuously or periodically over an extended time period, those skilled in the medical arts typically use what are known as "permanent" catheterization techniques. These techniques employ implanted devices such as tunneled central venous catheters (CVCs) that remain implanted for durations ranging from a few weeks to years. Examples of such implanted and related medical devices exist in the following references, which are incorporated herein by reference: U.S. Pat. No. 4,266,999 (Baier); U.S. Pat. No. 4,405,305 (Stephen et al.); U.S. Pat. No. 4,488,877 (Klein et al.); U.S. Pat. No. 4,668,222 (Poirier); U.S. Pat. No. 4,897,081 (Poirier et al.); U.S. Pat. No. 4,935,004 (Cruz); U.S. Pat. No. 5,098,397 (Svensson et al.); U.S. Pat. No. 5,100,392 (Orth et al.); U.S. Pat. No. 5,242,415 (Kantrowitz et al.); U.S. Pat. No. 5,662,616 (Bousquet); U.S. Pat. No. 5,823,994 (Sharkey et al.); U.S. Pat. No. 5,830,184 (Basta); U.S. Pat. No. 5,848,987 (Baudino et al.); U.S. Pat. No. 5,882,341 (Bousquet); U.S. Pat. No. 5,989,213 (Maginot); and U.S. Pat. No. 6,033,382 (Basta). Examples of therapeutic regimens requiring such long-term continuous or periodic access to a specific internal body location include parenteral feeding, chemotherapy, antibiotic administration, dialysis, and chronic anesthesiology. Central catheterization for these types of procedures are discussed in "Vascular Access for Oncology Patients" (Gallieni et al, *CA Cancer J Clin* 2008 doi: 10.3322/CA.208.0015).

Generally, the type of procedure that a patient requires dictates whether a physician will utilize an acute, short term catheterization technique, or a chronic, long term catheterization technique. For example, establishing a state of general anesthesiology in preparation for a surgical procedure typically involves placing a CVC in a patient's blood vessel for a relatively short period of time, such as a few minutes to a few hours, and then removing the catheter once the surgery is finished and the patient is revived. When performing such an anesthesiology procedure, a physician commonly uses a short term catheterization technique to place a drug delivery catheter in a blood vessel of the patient.

In direct contrast to this example of short term CVC placement, a physician performing a hemodialysis procedure in a patient suffering from chronic kidney failure may place a CVC in one of the patient's blood vessels for a relatively long period of time. Such a patient typically requires dialysis sessions three times per week for an indefinitely extended period of time. Healthy kidney function ensures removal of fluid, chemicals, and wastes typically filtered from a person's blood. Hemodialysis removes these elements by sending a patient's blood to an external artificial kidney machine via the permanent vascular access, often established by placement of a long term catheter within the patient. A patient who is involved in such a hemodialysis regimen may need a catheter placed in a blood vessel for weeks, months, or years in order to provide a ready means for vascular access into that patient's bloodstream to enable these frequent life saving dialysis treatments.

Long term catheterization techniques typically entail inserting a catheter into a patient using a "tunneled catheter technique." This procedure involves inserting a long term catheter into the patient through an incision in the skin and then routing the catheter for several centimeters under the skin before entering deeper regions of the body. Despite routine use, conventional tunneled catheter designs seriously compromise the ability of a patient's skin to protect the patient's body from infection. As discussed in "Intravascular Catheter-Related Infections: New Horizons and Recent Advances" (Raad et al., *Arch Internal Medicine*/Vol 162, Apr. 22, 2002, Pages 871-878.), catheter-related infections are frequent events and present a potentially fatal health problem. High morbidity rate and high procedural cost are characteristics of typical long term tunneled catheter usage. The primary reason that the use of conventional catheters leads to a high rate of infection is that microorganisms enter the body through the skin incision. A conventional tunneled catheter device may include a cylindrical tissue ingrowth cuff that acts as a barrier for micro-organisms entering the body and that anchors the catheter in the subcutaneous tunnel. Such a conventional device, however, still fails to prevent undesirably high infection rates. This is because standard cuff designs are designed for positioning within a subcutaneous tunnel rather than at the skin entry site, which is the most effective location at which to position a tissue ingrowth cuff for preventing infection.

Another conventional tunneled catheter design is entirely subcutaneous. This embodiment provides an advantage over traditional transcutaneous tunneled catheter designs by eliminating the need for a continuously maintained breach in skin and thereby reducing risk of infection. These subcutaneous catheters are connected to a port disposed beneath the skin. The port is capable of accepting a needle injection of fluid and then providing fluid to the subcutaneous catheter. The port has a compressed rubber septum on its upper surface immediately below the skin which is adapted for receiving a needle therethrough and resealing under residual compressive forces once the needle is removed. These fully subcutaneous devices present drawbacks relative to conventional transcutaneous catheter systems. Particularly, large bore needles would irreparably damage the septum, and so usage is limited to procedures that require low flow rates. An example of such an implanted, subcutaneous port and catheter device is provided in U.S. Pat. No. 5,562,618 (Cai, et al).

Some transcutaneous tunneled catheter devices include adjustable epidermal tissue ingrowth cuff assemblies that enable skin to heal into the devices at their entry sites into the dermis. Such devices provide reduced risk of infection, and because they require no needle punctures for gaining access to the catheter, these assemblies enable the higher flow rates associated with conventional transcutaneous tunneled catheter designs. For example, the apparatus and methods disclosed in U.S. Patent Application No. 2004/0236314 to Mark A. Saab (Saab), incorporated herein by reference, allow a physician to place a modular dermal tissue ingrowth cuff assembly precisely within a skin incision site and subsequently adjust the location of the distal (internal) tip of a catheter assembly associated with the tissue ingrowth cuff assembly. This device comprises a base (or port) having tissue ingrowth material thereon for securely anchoring the port at the incision site. A physician using such a device, therefore, has the ability to position the catheter tip precisely at the desired body site without disturbing, moving, or stressing the fixed tissue ingrowth cuff. Positioning the modular tissue ingrowth cuff at the skin incision site enables the skin to heal into the device and regain its ability to protect the patient from infection.

The use of a port with a transcutaneous catheter and skin tissue ingrowth cuff assembly has resulted in numerous improvements related to patient care and well being, but they do not anticipate or address the issue of simple and efficient removal of the port once the therapy has been completed and the device is no longer needed. U.S Publication Number 20070043323 to Davey and U.S. patent application Ser. No. 11/986,451 also to Christopher Davey address systems and methods for facilitating removal of subcutaneous tissue ingrowth devices. (Both of these references are incorporated herein by reference). The teachings in these references address the problem of tissue becoming too firmly ingrown into tissue ingrowth scaffolds, thereby requiring blunt dissection of the tissue from the device. The inventions of the Davey references comprise tissue ingrowth scaffolds that are at least partially bioabsorbable material and/or detachable from the device so that the scaffolds remain behind when the port is removed. These easily removed devices nonetheless require that a physician create a large incision through the skin to facilitate removal of the subcutaneous implanted device, regardless of the scaffold design or material. The need to make a large incision to enable removal of the subcutaneous implant significantly prolongs the procedure, greatly increases trauma to the patient, and exposes the patient to another risk of infection as a result of the added extensive breach to the skin.

A need therefore exists for a subcutaneous port that anchors a transcutaneous conduit during a treatment period and then enables removal through a minimally sized incision in the skin that causes little or no additional trauma to the patient.

SUMMARY OF THE INVENTION

The present invention comprises a medical device that is capable of implantation within a patient for long-term treatments, such as catheterization procedures, and a method of using the device. The implanted medical port of the present invention is capable of receiving, routing, and anchoring a treatment component, such as for example a fluid conduit, power cable, or fiber optic cable, that extends through the skin into the internal physiology of the patient. The port is shaped to maximize comfort, ease of installation, and stability after implantation, and thus a relatively flat or domed, and generally oval-shaped geometry is most preferable for placement and use.

In one embodiment of the implantable subcutaneous port for anchoring a transcutaneous treatment component, the implantable subcutaneous port comprises a body portion and one or more frangible lines formed within the body portion. The body portion is adapted for receiving the transcutaneous treatment component beneath the point of entry into the physiology of a patient and routing the transcutaneous treatment component. The body portion is produced from a deformable material and has an area footprint and defines a support wall through which the transcutaneous treatment component enters the body portion. Fracturing the one or more frangible lines formed within the body portion enables removal of the body portion from the physiology of a patient through a transcutaneous opening defining an area of less than thirty percent of the area footprint of the body portion.

In another embodiment, the port of the present invention further comprises at least one frangible line extending along a continuous path between an outer perimeter of the body portion and the support wall, and/or at least one gripping element disposed on the body portion at a point adjacent to the least one frangible line. Gripping the body portion and/or the at least one gripping element from a point external to the body of a patient and applying force outward from the major plane of the body portion results in fracturing the at least one frangible line along the continuous path between outer perimeter of the body portion and the annular support wall.

The present invention further comprises a method for removing a subcutaneous port for anchoring a transcutaneous treatment component. In one embodiment the method comprises removing the treatment component from the port, wherein the port comprises a body portion and one or more frangible lines formed within the body portion. The body portion is adapted for receiving the transcutaneous treatment component beneath the point of entry into the physiology of a patient and routing the transcutaneous treatment component. The body portion is produced from a deformable material and having an area footprint and defining a support wall through which the transcutaneous treatment component enters the body portion. Fracturing the one or more frangible lines formed within the body portion enables removal of the body portion from the physiology of a patient through a transcutaneous opening defining an area of less than thirty percent of the area footprint of the body portion.

Following the transcutaneous treatment component removal step, the method comprises inserting a retrieval implement through the transcutaneous opening, grasping the body portion with the retrieval implement near the one or more frangible lines, applying a force outward from the body portion so that the one or more frangible lines fracture, thereby sectioning the body portion into one or more pieces, and pulling the one or more pieces of the body portion through the transcutaneous opening.

These and other features and advantages of embodiments of the present invention are described in greater detail below with reference to the following figures.

BRIEF DESCRIPTION OF THE DRAWINGS

FIG. 7A depicts a perspective bottom view of an embodiment of the implantable subcutaneous port of the present invention during one stage of removal.

DETAILED DESCRIPTION

The present invention provides a medical device that is capable of implantation within a patient for long-term treatments. The device of the present invention includes a base, or port, that functions as an implanted medical port capable of receiving, routing, and anchoring a treatment component, such as for example a fluid conduit, power cable or fiber optic cable, that extends through the patient's skin into the patient's internal physiology. The port is deformable for facilitating removal. The port also is shaped to maximize comfort and ease of installation, and is relatively flat or dome shaped and has an oval-shaped or rounded geometry when viewed from the top. The port further may comprise at least one tissue ingrowth surface that helps further anchor the device and establish a biological seal between living tissue and the port.

Figure 1:
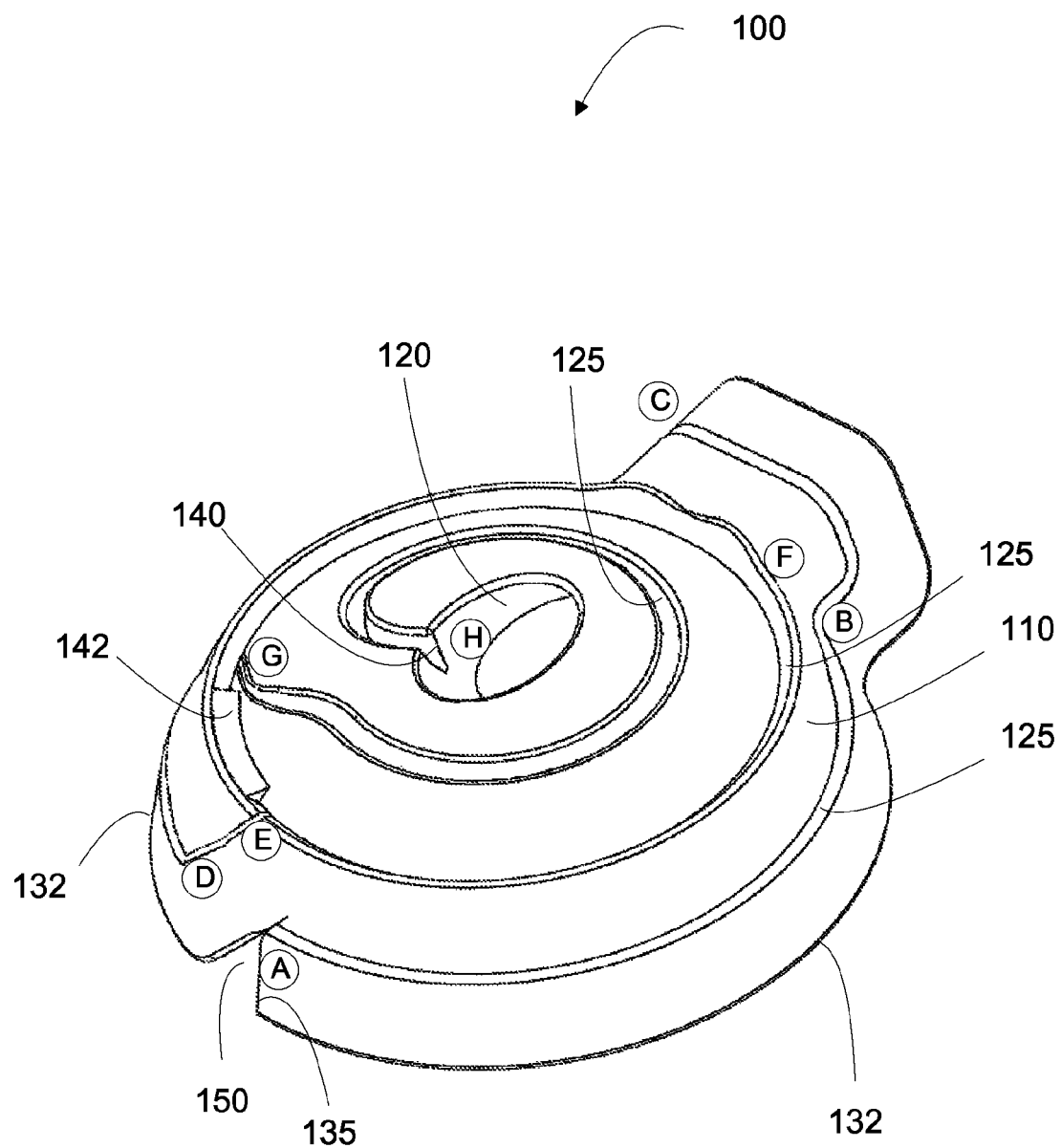
FIG. 1 depicts a perspective view of an embodiment of an implantable subcutaneous port of the present invention.
Figure 2:
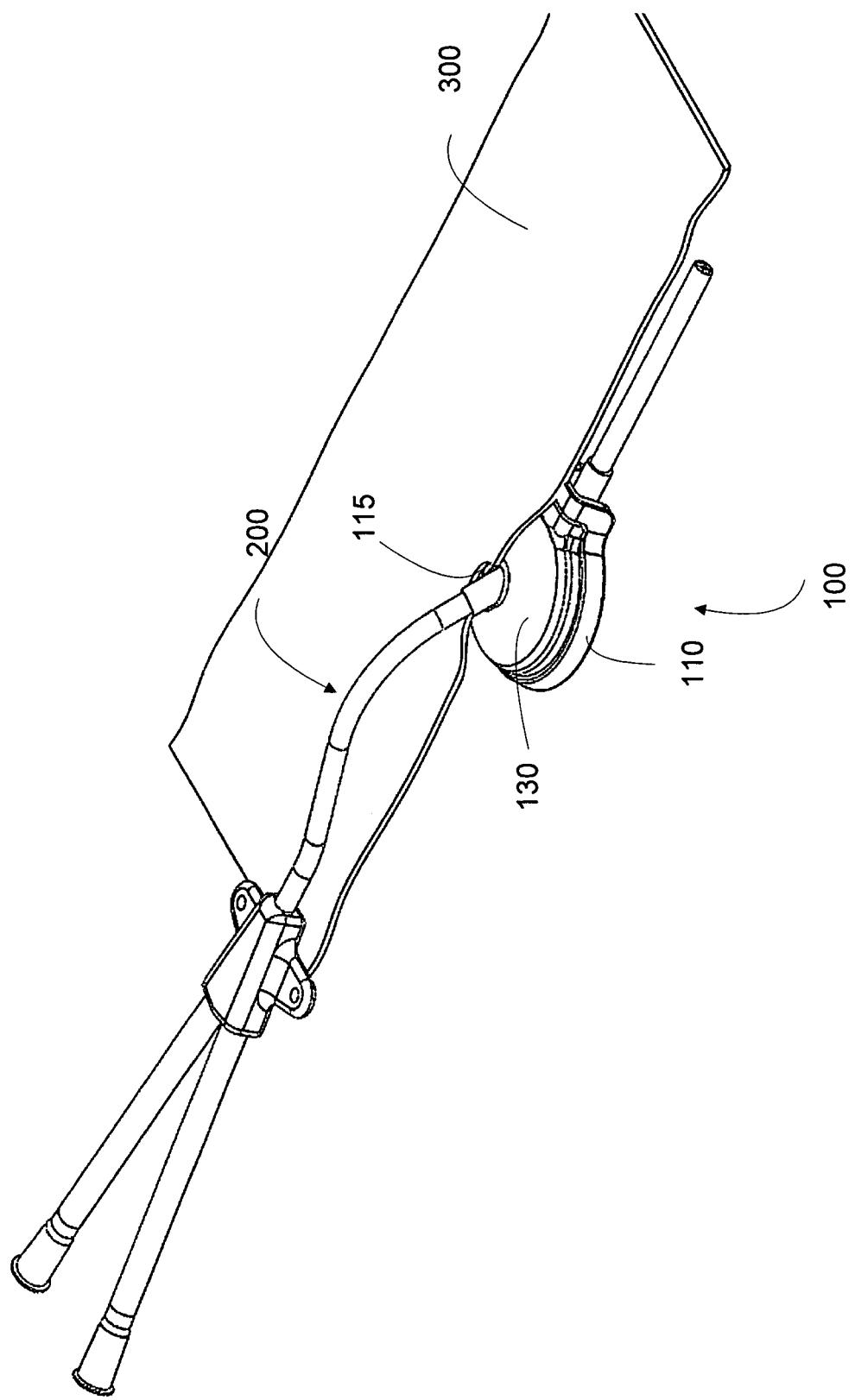
FIG. 2 depicts a perspective view of an embodiment of an implantable subcutaneous port of the present invention in use.
Figure 3:
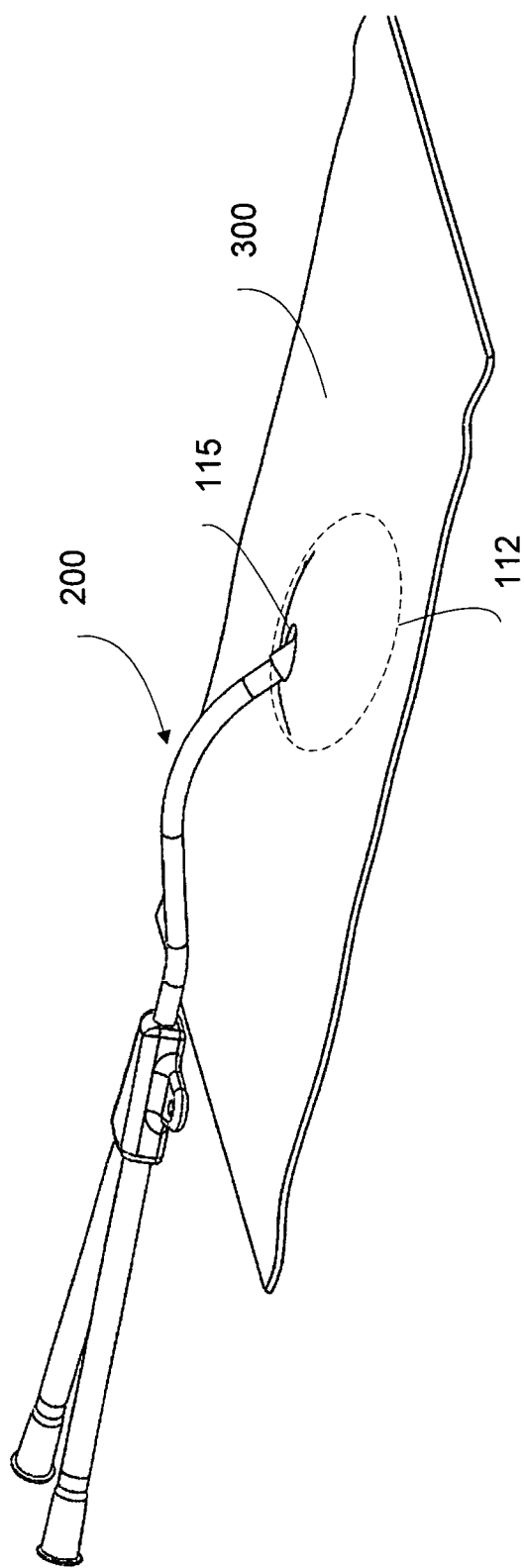
FIG. 3 depicts a perspective view of an embodiment of an implantable subcutaneous port of the present invention in use.

Taking FIGS. 1 through 3 together, one embodiment of the implantable subcutaneous port 100 of the present invention comprises a body portion 110 for anchoring a transcutaneous treatment component 200. In all embodiments, the body portion 110 may be dome shaped or flat. The body portion 110 receives the transcutaneous treatment component 200 beneath the point of entry 115, such as an incision in a dermal layer 300, and routes the transcutaneous treatment component into the physiology of the patient. The body portion 110 preferably is produced from a deformable polymer material for example, such as but not limited to, polyurethane, silicone, or any soft material having a durometer between 40 on the Shore A scale and 70 on the Shore D scale. The body portion 110 has an area footprint 112, and defines a support wall 120 through which the treatment component 200 enters the body portion 110. Like a conduit, the support wall defines an orifice through which the transcutaneous component passes. In one embodiment, the support wall is annular and defines a generally round orifice for accommodating a generally cylindrically shaped transcutaneous treatment component, but other embodiments may comprise an support wall defining a rectangle, hexagon, slit or any other geometric configuration suitable for the passage of a particularly shaped treatment component. The embodiment of the implantable subcutaneous port 100 of FIG. 1 comprises an annular support wall 120 defining a substantially round opening into the body portion 110. The support wall 120 is disposed at the top of the body portion 110 for positioning beneath the opening through the dermal layer 300 that defines the point of entry 115 of the transcutaneous treatment component 200.

Figure 4:
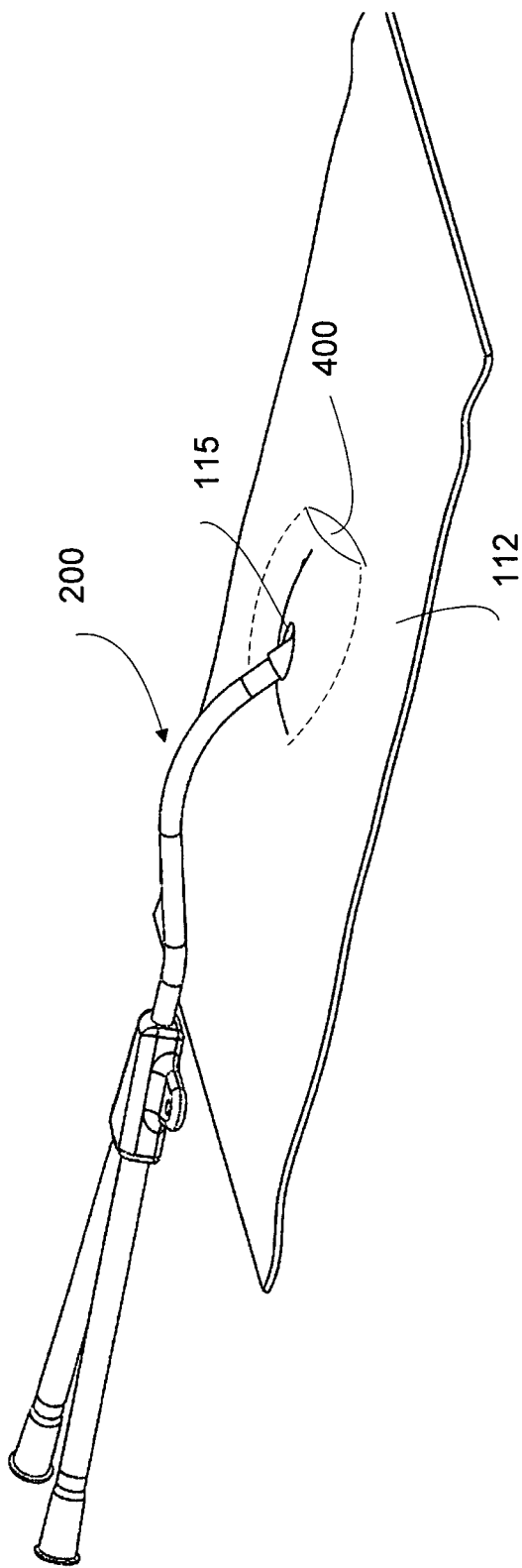
FIG. 4 depicts a perspective view of an embodiment of an implantable subcutaneous port of the present invention in use.
Figure 5A:
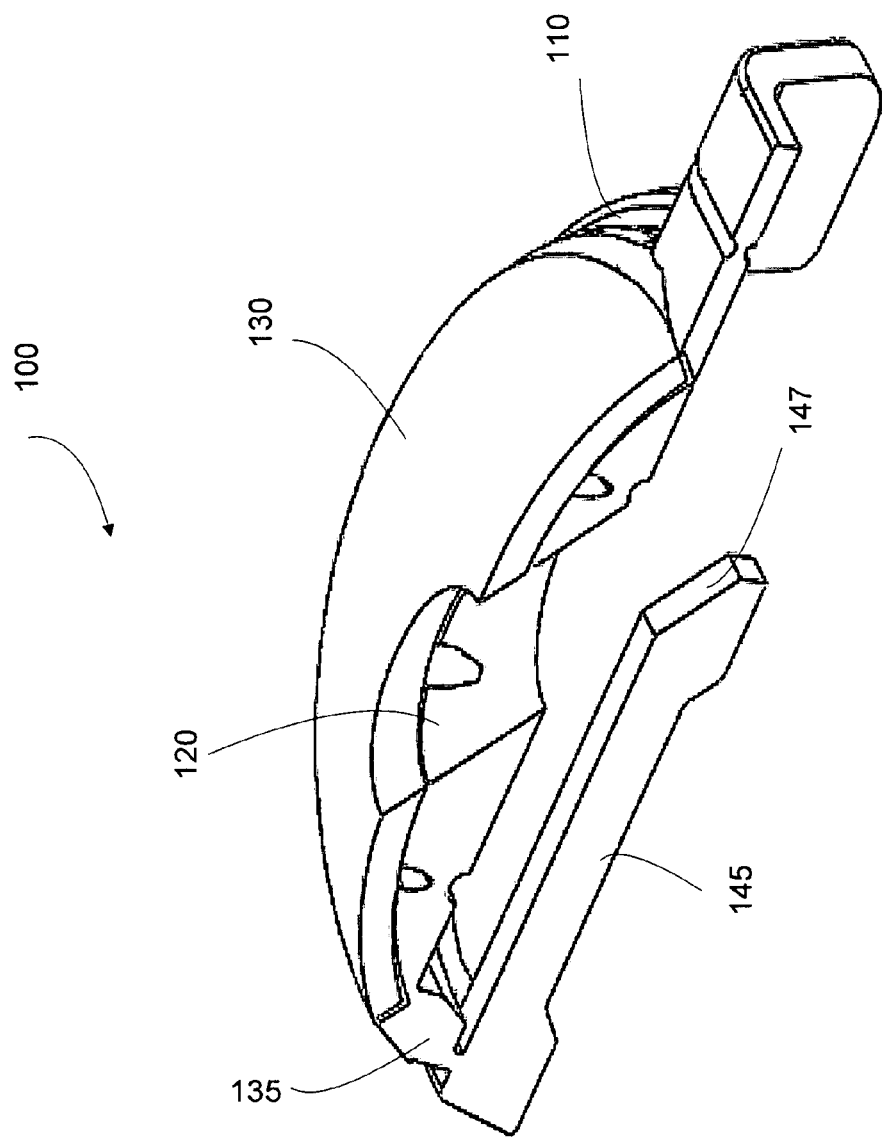
FIG. 5A depicts a perspective cross section of an embodiment of the implantable subcutaneous port of the present invention.
Figure 5B:
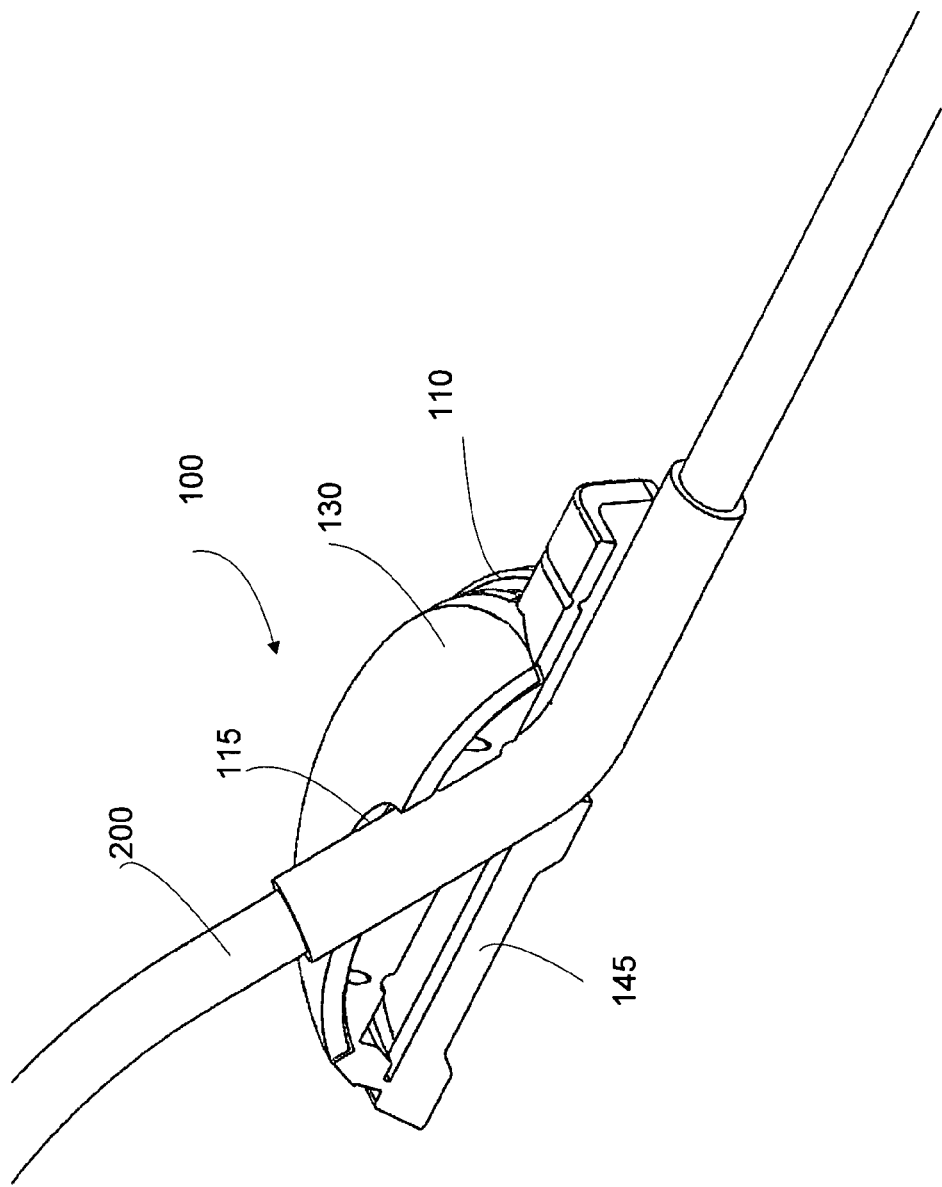
FIG. 5B depicts a perspective cross section of an embodiment of the implantable subcutaneous port of the present invention.

The implantable subcutaneous port 100 comprises one or more frangible lines 125 formed within the body portion, the fracture of which enables removal of the body portion 110 from the inner physiology of a patient through a transcutaneous opening defining an area of less than thirty percent of the area footprint 112 of the body portion 110. Furthermore, in some embodiments, the longest dimension of the transcutaneous opening is no more than 50 percent of the longest dimension of the major plane of the body portion. In one embodiment, the transcutaneous opening is the point of entry 115 of the transcutaneous treatment component 200. In another embodiment, the transcutaneous opening is an incision 400 adjacent the body portion 110, as indicated in FIG. 4. Preferably though, the length of the incision 400 is no more than 50 percent than the longest dimension of the body portion 110. For example, the embodiment of the body portion 110 of FIGS. 1A through 4 is generally round and has a longest dimension along its diameter. The length of an incision therefore would be no greater than half of the diameter of the body portion 110. Limiting the size of the incision 400 reduces the amount of trauma inflicted on the patient, thereby reducing the risk of infection.

Figure 8:
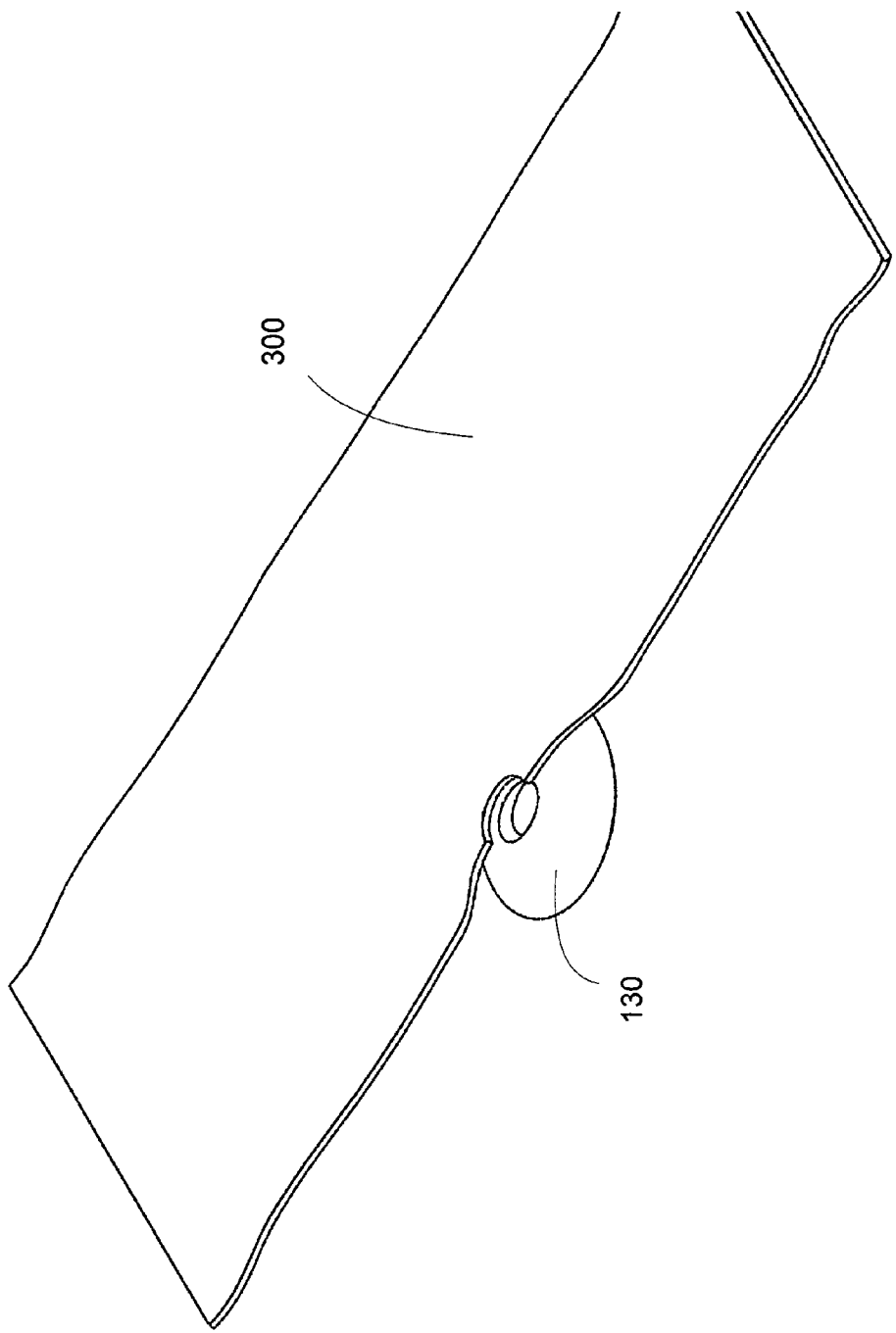
FIG. 8 depicts a top perspective view of a portion of one embodiment of the implantable subcutaneous port of the present invention.

The implantable subcutaneous port 100 may further comprise a tissue ingrowth skirt 130 made at least partially from a tissue ingrowth material and disposed the body portion about the support wall 120. This placement promotes tissue ingrowth into the tissue ingrowth skirt 130 around the point of entry 115 of the transcutaneous treatment component 200 so that a biological seal helps protect against infectious pathogens. In one embodiment the tissue ingrowth skirt may 130 be partially or completely bioabsorbable so that any portion remaining behind will safely degrade. In all embodiments having a tissue ingrowth skirt 130, following a period of tissue ingrowth, the force required to separate the body portion 110 from the tissue ingrowth skirt 130 is less than the force required to remove the tissue ingrowth skirt 130 from the dermal layer 300. This enables removal of the body portion 110 while leaving behind part or all of the tissue ingrowth skirt 130, as indicated in the embodiment depicted in FIG. 8.

Returning now to the configuration of the one or more frangible lines 125, placement of the one or more frangible lines 125 along the body portion 100 enables a clinician to fracture the body portion 110 into one or more lengths or sections for removal through a transcutaneous opening that is relatively smaller than the dermal incision required for placing the entire subcutaneous implantable port 100 at the outset of patient treatment. In certain embodiments, the body portion 110 is removable through the point of entry 115 of the transcutaneous treatment component 200 following removal of that element. Because of the elimination of any additional incision, such embodiments prevent a patient from enduring further trauma, and further reduce risk of infection and other risks associated with surgical procedures.

Figure 7B:
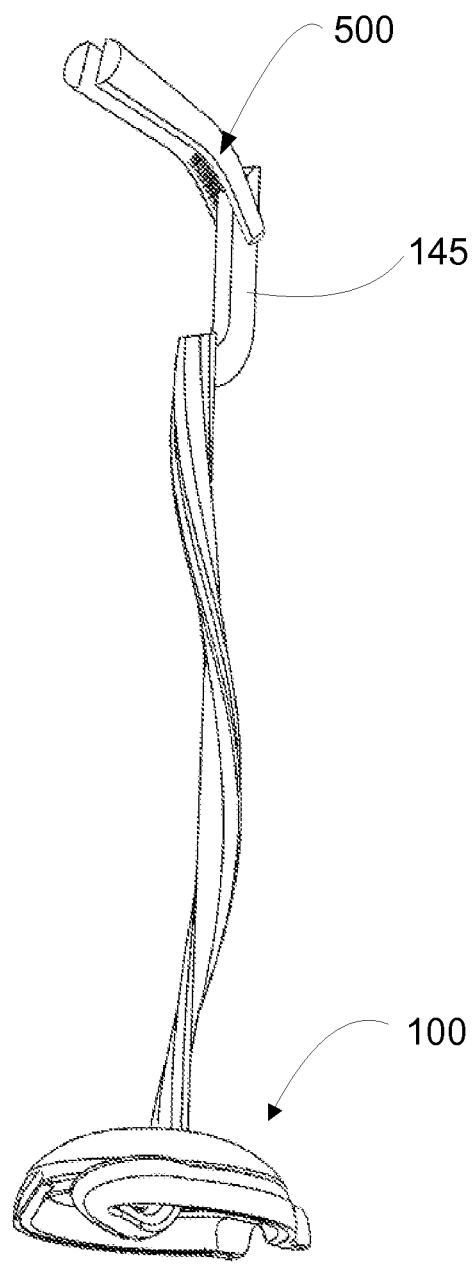
FIG. 7B depicts a perspective top view of an embodiment of the implantable subcutaneous port of the present invention during one stage of removal.
Figure 7C:
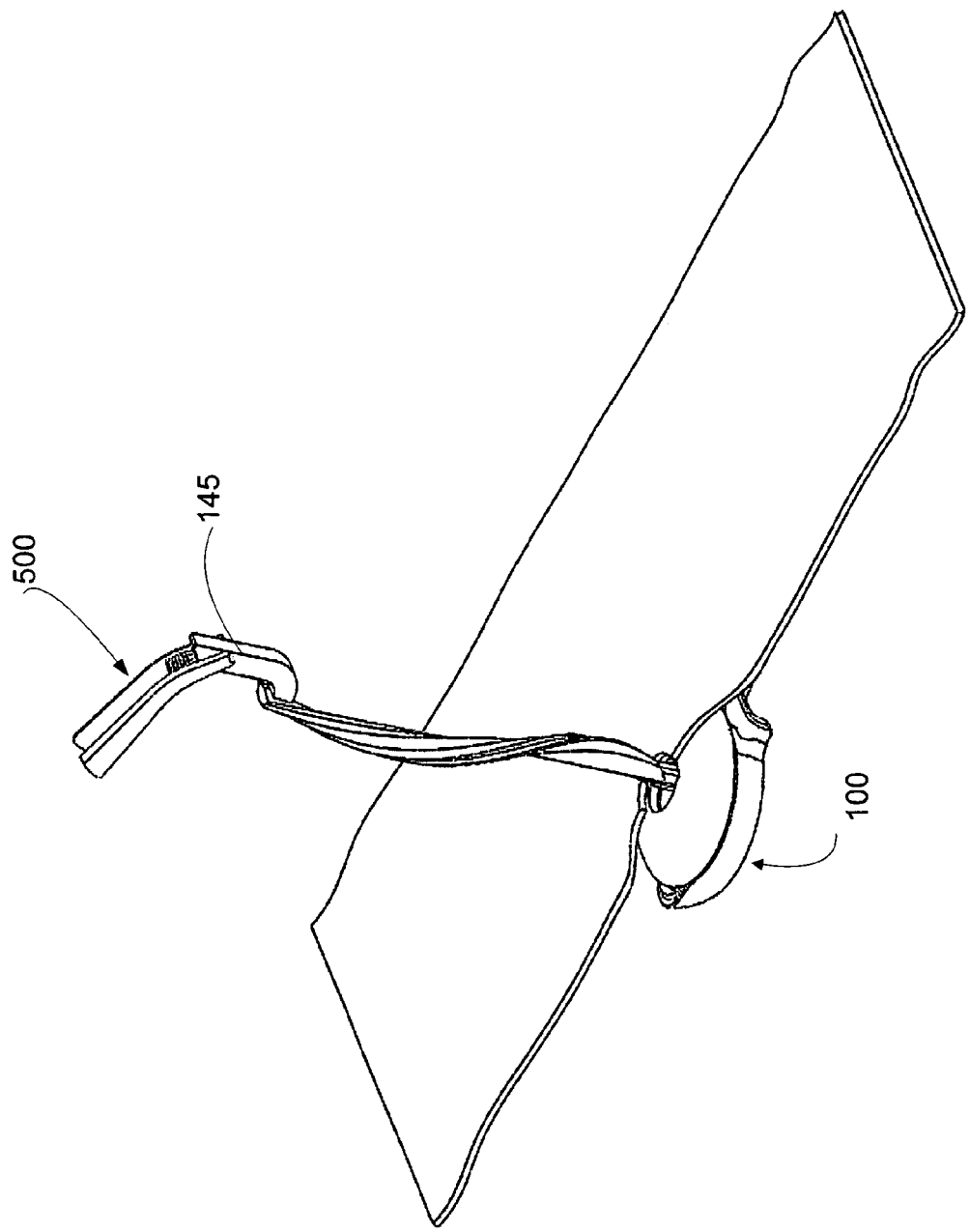
FIG. 7C depicts a perspective view of an embodiment of the implantable subcutaneous port of the present invention during one stage of removal.

In one embodiment, the one or more frangible lines 125 may form one or more paths extending between the support wall 120 and the outer perimeter 132 of the body portion 110 so that the body portion 110 is sectioned by the one or more frangible lines 125 into one or more removable pieces. The one or more paths of the one or more frangible lines 125 may be intersecting and/or non-intersecting so as to divide the body portion 110 into pieces sized for removal through a relatively small transcutaneous opening. In one embodiment, the one or more frangible lines form a continuous path extending between the support wall 120 and an outer perimeter 132 of the body portion 110. For example, in one embodiment shown in FIG. 1, the one or more frangible lines 125 may form one or more spirals wound around the orifice defined by the support wall 120 and spanning between the support wall 120 and the outer perimeter 132. This embodiment enables a clinician to fracture the body portion 110 along the one or more frangible lines 125 and uncoil the body portion 110 for removal in long, thin strips, as depicted fore example in FIGS. 7A through 7C. In yet another embodiment (not shown), the one or more frangible lines 125 form one or more paths across the major plane of the body portion 110, extending between two points on the outer perimeter and thereby sectioning the body portion 110 into two or more adjacent strips.

In still yet another embodiment (not shown), the body portion 110 is dome shaped and the one or more frangible lines 125 form one or more closed circuitous paths in the major plane of the body portion 110, thereby sectioning the body portion 110 into two or more stacked sections. In a similar embodiment (not shown) the body portion 110 is substantially flat and the one or more frangible lines 125 form one or more closed circuitous paths in the major plane of the body portion 110, thereby sectioning the body portion 110 into two or more nested sections. Because the body portion 110 is made from a deformable material, the two or more stacked or nested sections are at least partially collapsible for facilitating removal through a transcutaneous opening having an area no larger than 30 percent of the area footprint 112. In embodiments where the body portion 110 is removed through the point of entry 115 of the transcutaneous treatment component 200, the area of that transcutaneous opening may be a little as 10 to 15 percent of the area footprint 112 of the body portion 110.

As indicated in FIG. 1, in certain embodiments, the one or more frangible lines 125 each have a pulling end 135 and a terminal end 140. The pulling end 135 enables a clinician to initiate a tear along the one or more frangible lines 125 at a particular graspable point on the body portion 110. The embodiment of FIG. 1 also comprises a stiffener 142 disposed on the body portion 110 between the pulling end 135 and the terminal end 140. The stiffener 142 may be a localized thickening of the body portion 110 or an appended element disposed on and integrated with the body portion 110 for assisting with directing tear propagation along the one or more frangible lines 125. In effect, the stiffener 142 prevents shearing or tearing along an area of the body portion 110 located between two relatively closely-spaced portions of the one or more frangible lines 125. For example, in the embodiment of FIG. 1, tearing begins at the pulling end 135 along the one or more frangible lines 125 in the direction of location A. The tear propagates to location B and location C, wraps around the body portion 110 and turns a sharp corner between D and E. At point E, the tear could propagate in either of two directions if not for the presence of the stiffener 142. The stiffener 142 prevents tearing in an undesired direction and forces propagation of the tear in the direction of points F, G and eventually H, located at the terminal end 140. In the embodiment of FIG. 1, the stiffener 142 therefore assists with fully unraveling the body portion 110 for easy removal in one long, narrow strip.

In some embodiments, the implantable subcutaneous port 100 further comprises a gripping element 145 disposed on body portion 110 adjacent the pulling end 135, as depicted in FIGS. 5A through 7C. In the embodiment of FIGS. 5A through 7C, the gripping element 145 extends within the area footprint 112 of the body portion 110, starting at an outer perimeter 132 of the body portion and extending up to an inserted transcutaneous treatment component 200. In the embodiment of FIGS. 5A through 7C, the gripping element 145 extends from the outer perimeter 132 of the body portion 110, but, alternatively, the gripping element 145 may extend from any point on the body portion 110. For example, the gripping element 145 may be disposed on the body portion 110 at a point located directly beneath the support wall 120 for increased accessibility as compared to the embodiment placing the gripping element 145 closer to the outer perimeter 132 and therefore deeper within the physiology of the patient. In still yet another embodiment, the gripping element may extend beyond the area footprint 112 of the body portion 110.

Figure 9A:
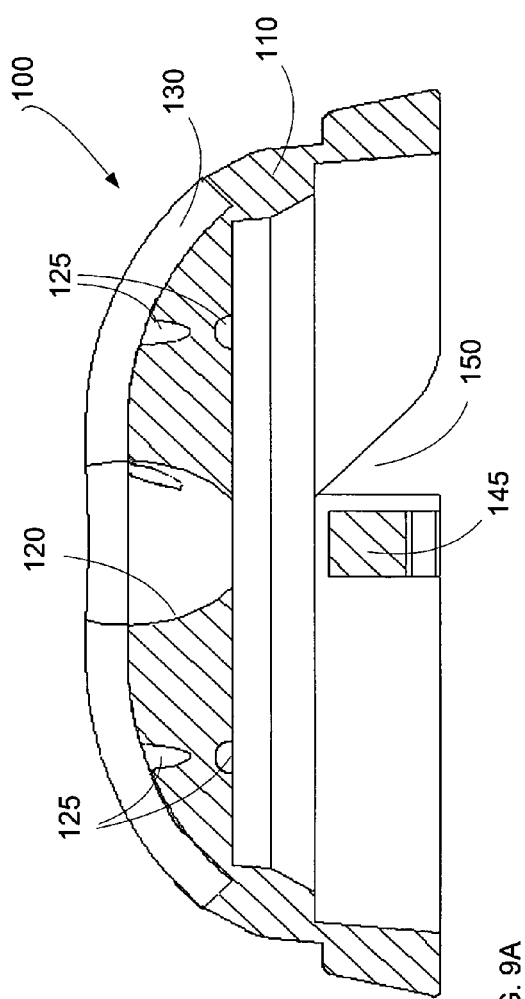
FIG. 9A depicts a cross-sectioned end view of one embodiment of the implantable subcutaneous port of the present invention.
Figure 9B:
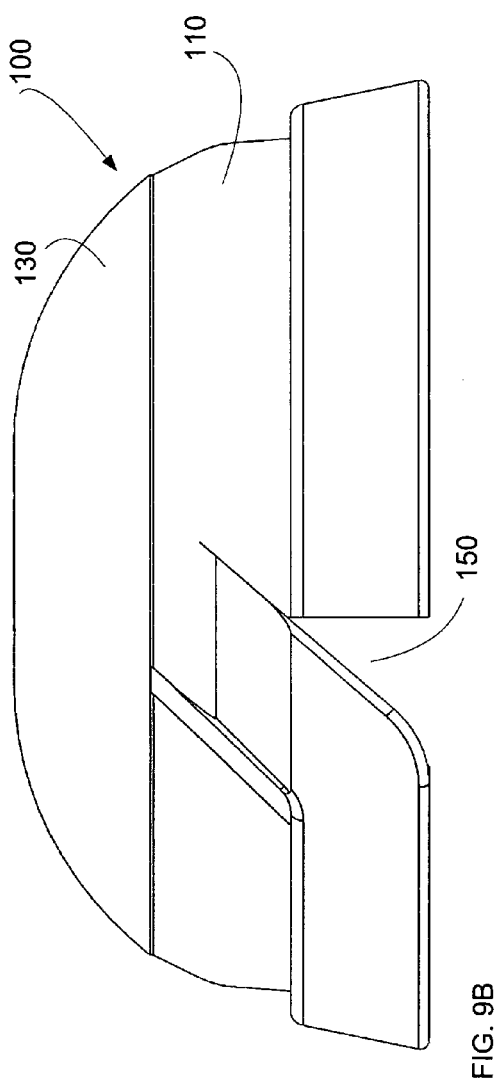
FIG. 9B depicts an end view of one embodiment of the implantable subcutaneous port of the present invention.

In some embodiments, the gripping element 145 may terminate in a contoured end 147 for accommodating the contours of the adjacent transcutaneous treatment component 200 and/or for assisting with directing the treatment component into the physiology of a patient. In the embodiment of FIGS. 5A through 7C, the gripping element 145 terminates at a contoured end 147 reachable through the orifice defined by the support wall 120. As FIG. 5B clearly depicts, the contoured end 147 directs an inserted treatment component through the body portion 110 at a proscribed angle. Following removal of the treatment component, a clinician may insert a retrieval implement 500, such as forceps or tweezers, through the support wall 120 for grasping the gripping element 145 and pulling that gripping element 145 up through the support wall 120 and out of the a patient with the unraveling body portion 110 in tow. Gripping the gripping element 145 from a point external to the physiology of a patient and applying a force outward from the major plane of the body portion 110 therefore results in fracturing the one or more frangible lines 125 and unraveling the body portion 110 along those one or more frangible lines 125. Applying a slight torque or twisting motion during the application of outward force may assist in fracturing the one or more frangible lines 125. In some embodiments, a notch 150 disposed near the pulling end 135 and adjacent the intersection of the pulling end 135 and the gripping element 145 may assist with the initial propagation of a tear along the frangible line 125. FIGS. 9A and 9B depict such an embodiment.

Alternatively, in certain embodiments (not shown), the body portion 110 may comprise one or more puncture points, or relatively thin wall sections, that enable a clinician to puncture the body portion 110 with an implement at a point near the one or more frangible lines 125. The clinician then may grasp the wall of the body portion 110 with the retrieval implement 500, and pull on the body portion 110 to initiating a tear along the one or more frangible lines 125. This puncture technique may be particularly useful in embodiments such as those described above having one or more frangible lines 125 forming closed circuitous paths in the body potion 110 and thereby separating the body portion 110 into two or more stacked sections. Those embodiments, however, may benefit from the inclusion of one or more gripping elements 145 as well. In all embodiments, the gripping element 145 may be disposed on the body portion 110 so that tears propagate along the one or more frangible lines 145 in more than one direction, starting from the point of intersection of the gripping element 145 (or puncture point) and the one or more frangible lines 145. Additionally, some embodiments of the body portion 110 may further comprise radiopaque or ultrasonically detectable markers disposed at various points along the body portion 110 to enable a clinician to determine whether or not the entire body portion 110 has been successfully removed.

As described above, the body portion 110 is made of a material having a durometer that enables fracturing along the one or more frangible lines 125 under an application of force and that enables a sufficient amount of deformation for removal of the body portion 110 in one or more sections delineated by the one or more frangible lines 125. Spacing between the one or more frangible lines 125 is adjustable in accordance with material selection and, in particular, material elasticity. A proper combination of material selection and spacing between the one or more frangible lines 125 prevents shearing or yielding of the unraveling section of the body portion 110 under an application of force required for removal through a relatively small transcutaneous opening, such as the point of entry 115 of the transcutaneous treatment component into the physiology of a patient.

One skilled in the art could form the one or more frangible lines 125 within the body portion 110 using numerous manufacturing techniques. For example, the body portion 110 may be injection molded with the one or more frangible lines 125 cast therein, or the one or more frangible lines 125 may be etched into the formed body portion 110. In certain embodiments, the one or more frangible lines 125 oppose one another and are formed on both the top surface and the underside surface of the body portion 110, such that a reduction in thickness occurs from both sides. This type of manufacture is indicated, for example, in the cross section view of the embodiment of the implantable subcutaneous port 100 depicted n FIG. 9A. In addition to applying injection molding and etching techniques, selective weakening of the body portion 110 along the one or more frangible lines 125 also could be accomplished by other means including, but not limited to, serial perforation, chemical etching, mechanical skiving, mechanical scoring, or other methods known to those skilled in the art. The one or more frangible lines 125 could be formed using a localized heat treatment that changes the crystalline structure of the material along the one or more frangible lines 125, thereby reducing required shear forces required to tear the body portion 110 at those specific locations.

One skilled in the art also could apply heat treatments to reflow the material of the body portion 110 to form a berm on either side of the one or more frangible lines 125, thereby creating a larger gradient between the force required to shear the body portion 110 generally and the force required to shear the body portion 110 along the one or more frangible lines 125. In another embodiment, one skilled in the art could injection mold such a berm into the body portion 110 along at least select sections of the one or more frangible lines 125, thereby providing further directional control over tear propagation. In some embodiments, localized thickening of the body portion 110 on either side, both sides, or alternating sides of the one or more frangible lines 125 provides further directional control over tear propagation along the one or more frangible lines 125. In yet another embodiment, the body portion 110 further comprises materials that are highly degradable and/or bioabsorbable in localized areas. In this embodiment, the body portion 110 has a substantially uniform wall thickness during initial placement within the physiology of a patient, but, over time, the degradable or absorbable material weakens the body portion 110 in localized areas, thereby creating one or more frangible lines 125.

Figure 10:
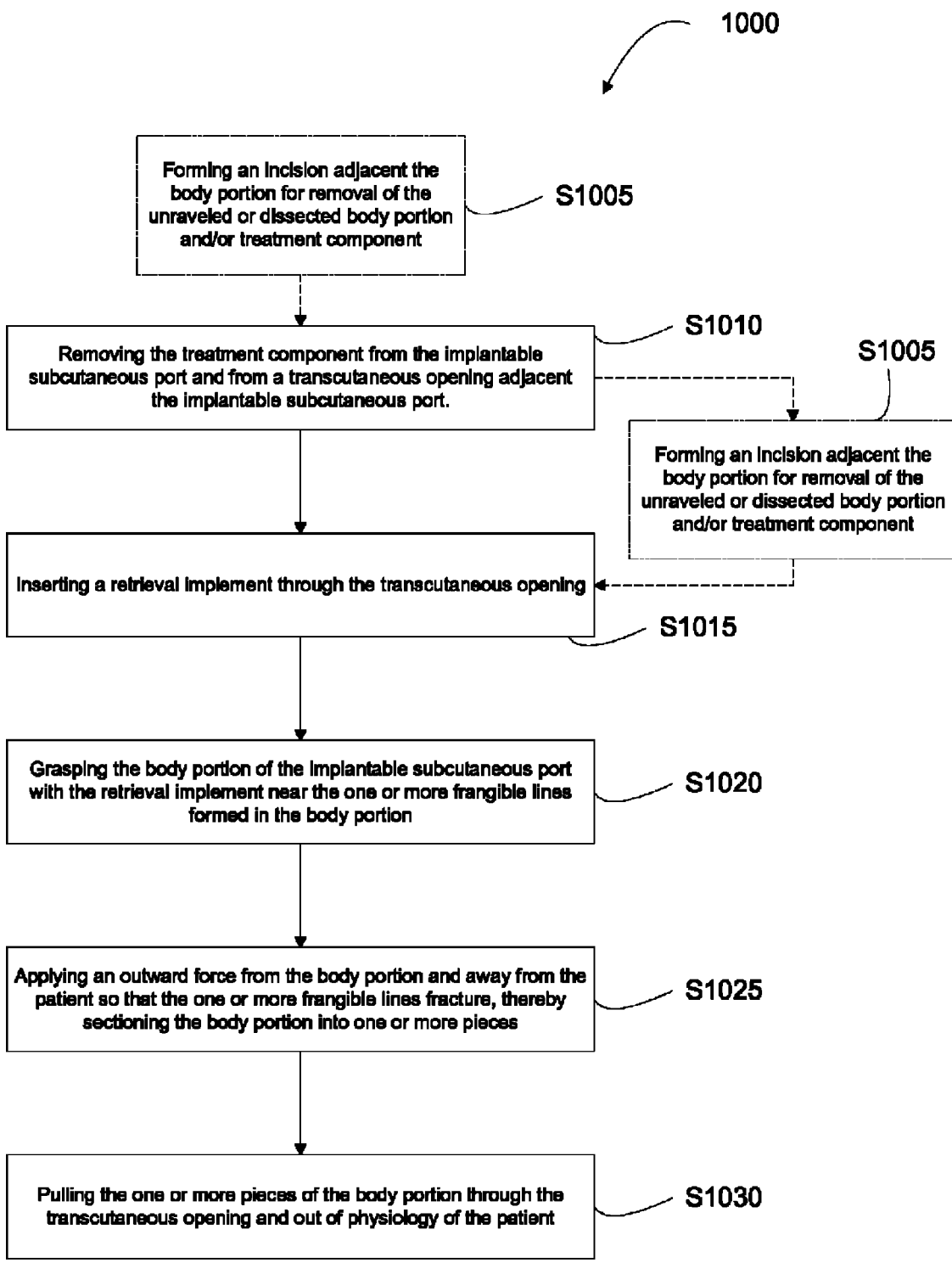
FIG. 10 depicts a schematic of one embodiment of a method of removing an implanted subcutaneous port.

Turing now to FIG. 10, the present invention also comprises a method of removing 1000 an implantable subcutaneous port 100 for anchoring a transcutaneous treatment component 200. In a first step S1010, the method of removing 1000 comprises removing the treatment component 200 from the implantable subcutaneous port 100 and from a transcutaneous opening adjacent the port. The implantable subcutaneous port 100 comprises a body portion 110 for receiving the transcutaneous treatment component 200 beneath the point of entry 115 into the physiology of a patient. The body portion 110 is formed from a deformable material and has an area footprint 112 defined by the outer perimeter 132 of the implantable subcutaneous port 100. The body portion 110 comprises a support wall 120 defining an orifice through which the transcutaneous treatment component 200 enters into the body portion 110, which further routes the treatment component 200 into the physiology of the patient. Additionally, the implantable subcutaneous port 100 comprises one or more frangible lines 125 formed within the body portion 110, the fracture of which enables the removal of the body portion 110 from the physiology of a patient through a transcutaneous opening, such as the point of entry 115 of the transcutaneous treatment component 200. A clinician may remove the body portion 110 through an alternate transcutaneous opening, such as an incision 400 in the dermal layer 300 adjacent the body portion 110. In any embodiment, the transcutaneous opening typically spans an area of less than thirty percent of the area footprint 112 of the body portion 110.

Figure 6:
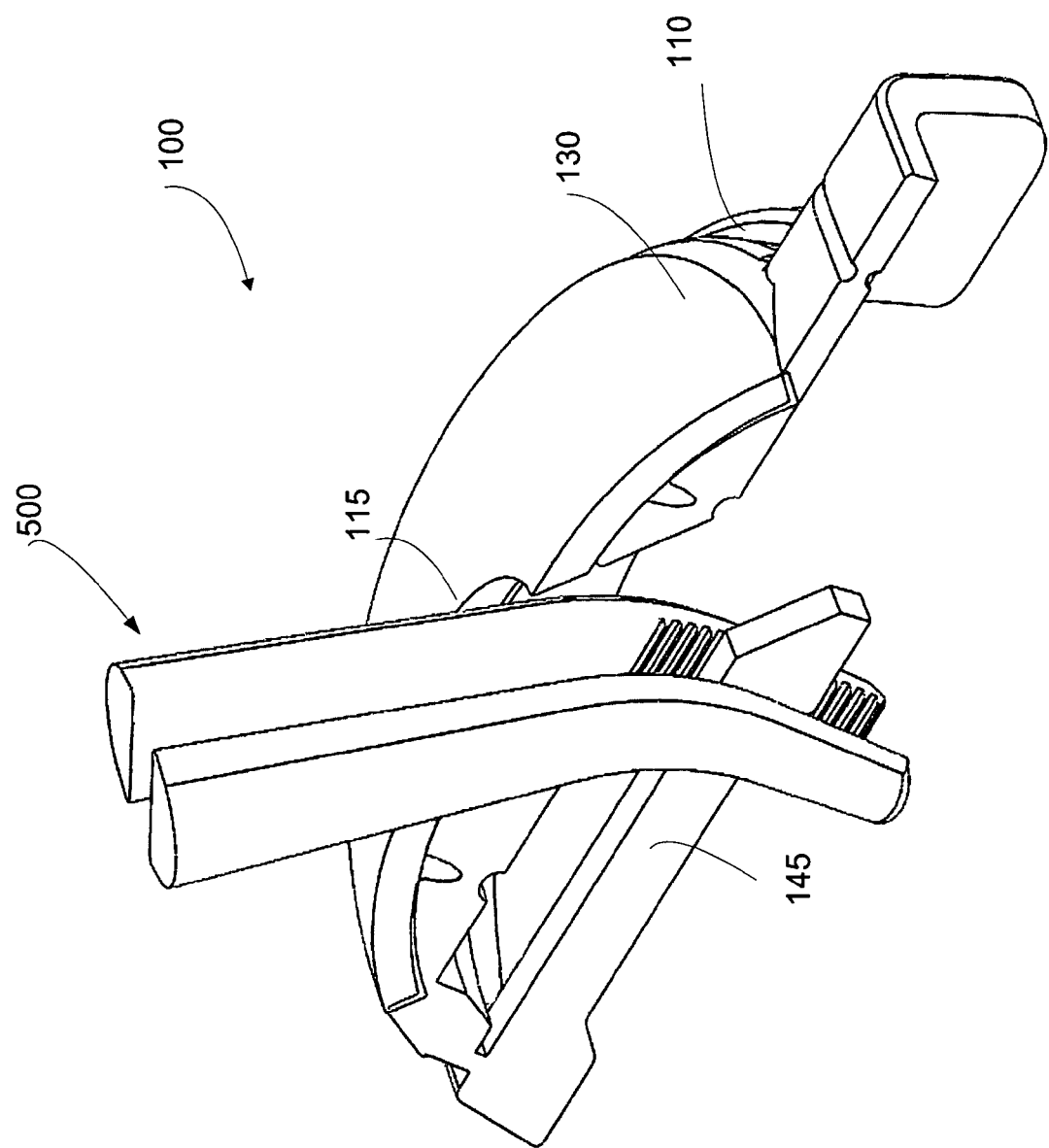
FIG. 6 depicts a perspective cross section of an embodiment of the implantable subcutaneous port of the present invention

Turning back to the method of removing 1000 the implantable subcutaneous port 100, a second step S1015 comprises inserting a retrieval implement 500 through the transcutaneous opening, and a third step S1020 comprises grasping the body portion 110 with the retrieval implement 500 near the one or more frangible lines 125. As depicted in FIG. 6, the body portion 110 may further comprise a gripping element 145 disposed adjacent to the one or more frangible lines, wherein gripping the gripping element 145 from a point external to the physiology of a patient and applying force outward from the major plane of the body portion 110 results in fracturing the one or more frangible lines 125. The method of removing 1000 may further comprise an incising step S1005 prior to and/or following the first step S1010 of removing the treatment component. The optional incising step S1005 comprises a clinician forming an incision adjacent the body portion 110 for removal of the unraveled or dissected body portion 110 and/or the treatment component 200.

Fracturing of the one or more frangible lines 125 resizes the body portion into one or more sections sized for removal through the transcutaneous opening, which has a longest dimension no greater than fifty percent of the longest dimension of the area footprint 112. The one or more frangible lines 125 may be configured in any number of patterns as described above with regard to embodiments of the implantable subcutaneous port 100. In an alternate embodiment, also described above, the body portion 110 comprises no gripping element 145, but instead comprises one or more areas of weakness defined by thinned wall sections disposed adjacent the one or more frangible lines 125. A clinician may puncture the body portion 110 in these one or more areas of weakness with a retrieval implement 500 and then grasp the wall of the body portion 110 while applying an outward force to propagate a tear along the one or more frangible lines 125 and in one or more directions from the point of puncture initiation.

Returning to the method of removing 1000, a fourth step S1025 comprises applying a force outward from the body portion 110 and away from the patient so that the one or more frangible lines 125 fracture, thereby sectioning the body portion 110 into one or more pieces. As further indicated in the embodiment of FIGS. 7A through 7C, pulling the gripping element 145 further away from the body portion 110 further unravels and removes the portion of the body portion 110 attached to the gripping element 145. The method of removing 1000 comprises a final step S1030 of pulling the one or more pieces of the body portion 110 through the transcutaneous opening, here the point of entry 115, and out of the physiology of the patient. In certain embodiments, the method of removing 1000 further comprises separating the body portion 110 from all or part of a tissue ingrowth skirt 130 disposed thereon for promoting tissue ingrowth around the point of entry 115 of the transcutaneous treatment component 200. For example, in the embodiment depicted in FIGS. 7A through 8, the body portion 110 unravels, leaving behind the entire tissue ingrowth skirt 130 under the dermal layer 300.

Preferably, this tissue ingrowth skirt 130 is also biodegradable and/or bioabsorbable so that the physiology of the patient dissolves and clears the tissue ingrowth skirt 130 over time. In alternate embodiments the tissue ingrowth skirt 130 can be made of a material that is suitable for use as a permanent implant, such a polyester velour fabric, which is used on a wide range of permanently implanted medical devices.

It is noted that the foregoing examples have been provided merely for the purpose of explanation and are in no way to be construed as limiting of the present invention. While the present invention has been described with reference to an exemplary embodiment, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

I claim:

1. An implantable subcutaneous medical device for anchoring an elongated transcutaneous treatment component that, in use, extends from outside a patient's skin, through a transcutaneous skin opening sized to just accommodate the treatment component at a point of entry into the physiology of a patient, through the implanted medical device positioned at an implantation site, and then to a desired internal location in the patient's body distal of the implanted medical device, the device comprising:
   a) a device body portion having a passageway therethrough comprising a passageway entrance and support wall for receiving the transcutaneous treatment component beneath the point of entry and for subcutaneously routing the transcutaneous treatment component to the desired internal location, the device body portion being produced from a deformable material and having an assembled area footprint; and,
   b) one or more frangible lines formed within the device body portion, the fracture of which enables in situ disassembly of the device body portion into one or more device body pieces sized in at least one dimension for removal from the physiology of the patient through the transcutaneous skin opening.

2. The medical device of claim 1 wherein the support wall is annular.

3. The medical device of claim 1 further comprising a tissue ingrowth skirt disposed on a surface of the device body portion about the passageway entrance for promoting tissue ingrowth at least about the passageway entrance and the portion of the transcutaneous treatment component that passes through the passageway entrance.

4. The medical device of claim 1 wherein the longest dimension of the transcutaneous skin opening is no more than 50 percent of the longest dimension of the major plane of the device body portion.

5. The medical device of claim 1 wherein the one or more frangible lines form a continuous path extending between the support wall and an outer perimeter of the device body portion.

6. The medical device of claim 5 wherein the continuous path forms a spiral along the device body portion.

7. The medical device of claim 1 wherein the device body portion is dome shaped.

8. The medical device of claim 7 wherein the one or more frangible lines form one or more closed circuitous frangible line paths in a major plane of the device body portion thereby defining two or more stacked device segments.

9. The medical device of claim 1 further comprising a device gripping element disposed on a wall of the device and extending within the assembled area footprint of the device body portion, whereby the device gripping element can be accessed from a point external to the physiology of a patient through the transcutaneous skin opening and/or the passageway after removal of the transcutaneous treatment component such that applying force to the device gripping element results in fracturing the one or more frangible lines.

10. The medical device of claim 1 wherein the device body portion is generally disc shaped.

11. The medical device of claim 1 wherein the one or more frangible lines form one or more closed circuitous frangible line paths in a major plane of the device body portion thereby defining two or more nested device segments.

12. The medical device of claim 1 wherein the one or more frangible lines form one or more frangible line paths across major planes of the device body portion, extending between two points on the outer perimeter of the device thereby defining two or more device segments.

13. The medical device of claim 12 wherein the one or more frangible line paths are non-intersecting.

14. The medical device of claim 12 wherein the one or more frangible line paths intersect.

15. The medical device of claim 1 wherein each frangible line comprises a pulling end and a terminal end.

16. The medical device of claim 15 further comprising a device gripping element disposed at the pulling end of a frangible line and extending within the assembled area footprint of the device body portion.

17. The medical device of claim 15 further comprising an access point adjacent the pulling end of a frangible line for accessing the pulling end to initiate a tear along one or more of the frangible lines.

18. The medical device of claim 17 wherein the access point is a relatively thinner section of the device body portion.

19. The medical device of claim 15 further comprising a notch adjacent the pulling end of a frangible line for assisting in propagating a fracture along the frangible line.

20. A medical device according to claim 1 wherein the device pieces are sized for removal through a transcutaneous skin opening that is smaller than the size of an incision required for implanting the assembled device body portion.

21. A medical device according to claim 1 wherein the device pieces are sized for removal through a transcutaneous skin opening that defines an area of less than thirty percent of the assembled area footprint of the assembled device body portion.

22. A medical device according to claim 1, wherein a frangible line formed within the device body portion forms a continuous spiral path extending between the passageway support wall and an outer perimeter of the device body portion such that fracturing the frangible line produces a long, thin ribbon of material that unravels in situ and can be removed from the implantation site through the transcutaneous skin opening.

23. A medical device according to claim 1, wherein the device further comprises a tissue ingrowth skirt disposed along a surface of the device body portion around the point of entry of the transcutaneous treatment component, which skirt either entirely remains in place under the dermal layer adjacent the implantation site when the device body portion is disassembled and removed, or which skirt is biodegradable and/or bioabsorbable so that the physiology of the patient dissolves and clears the tissue ingrowth skirt.

24. An implantable subcutaneous medical device for anchoring an elongated transcutaneous treatment component that, in use, extends from outside a patient's skin, through a transcutaneous skin opening sized to just accommodate the treatment component at a point of entry into the physiology of a patient, through the implanted medical device positioned at an implantation site, and then to a desired internal location in the patient's body distal of the implanted medical device, the device comprising:
 a) a device body portion having a passageway therethrough comprising a passageway entrance and support wall for receiving the transcutaneous treatment component beneath the point of entry and for subcutaneously routing the transcutaneous treatment component to the desired internal location, the device body portion being produced from a deformable material and having an assembled area footprint;
 b) at least a frangible line extending along a continuous path between an outer perimeter of the device body portion and the annular support wall; and
 c) at least one device gripping element disposed on the device body portion at a point adjacent to the frangible line,
 whereby gripping the gripping element from a point external to the body of a patient and applying force results in fracturing the frangible line along the continuous path enabling removal of the device body portion from the body of the patient through a transcutaneous skin opening defining an area of less than thirty percent of the assembled area footprint.

25. An implantable subcutaneous medical device comprising a device body portion as follows:
 a) said device body portion comprises at least two wall sections transverse relative to one another, the wall sections together defining a device interior region, further wherein two transverse wall sections include apertures extending through the wall sections into the device interior region such that an elongated transcutaneous treatment component can be passed through the aperture of one wall section, through the device interior region, and out through the aperture of the other wall section; and,
 b) said device body portion further comprises one or more frangible lines formed within the device body portion such that fracturing the device body portion along the frangible lines causes in situ disassembly of the device body portion into one or more device pieces sized in at least one dimension for removal from a subcutaneous implantation site in a patient through a minimally-sized removal incision in the patient's skin that is smaller than a dimension of the device body portion along any axis prior to disassembly of the device body portion.

26. The medical device of claim 25 wherein the device pieces are sized for removal through a removal incision in a patient's skin that defines an area of less than thirty percent of the area footprint of the assembled device body portion.

27. A medical device according to claim 25, wherein a frangible line formed within the device body portion forms a continuous spiral path extending between the aperture of a wall section and the wall section having the other aperture such that fracturing the frangible line produces a long, thin ribbon of material that unravels in situ and can be removed from the implantation site through the removal incision.

28. A medical device according to claim 25, wherein the device further comprises a tissue ingrowth skirt disposed along a wall section of the device body portion around the point of entry of the transcutaneous treatment component, which skirt either entirely remains in place under the dermal layer adjacent the implantation site when the device body portion is disassembled and removed, or which skirt is biodegradable and/or bioabsorbable so that the physiology of the patient dissolves and clears the tissue ingrowth skirt.

29. The medical device of claim 25 wherein the longest dimension of the removal incision is no more than 50 percent of the longest dimension of the major plane of the device body portion.

30. The medical device of claim 25 wherein the device body portion is dome shaped.

31. The medical device of claim 25 further comprising a device gripping element disposed on a wall section and extending into the device interior region, whereby the device gripping element can be accessed from a point external to the physiology of a patient through the removal incision and/or the aperture of a wall section after removal of the transcutaneous treatment component such that applying force to the device gripping element results in fracturing the frangible line(s).

32. The medical device of claim 25 wherein the device body portion is generally disc shaped.

33. The medical device of claim 25 wherein the frangible lines are non-intersecting.

34. The medical device of claim 25 wherein at least two of the frangible lines intersect.

35. The medical device of claim 25 wherein each frangible line comprises a pulling end and a terminal end.

36. The medical device of claim 35 further comprising a device gripping element disposed at the pulling end of a frangible line and extending into the device interior region.

37. The medical device of claim 35 further comprising an access point adjacent the pulling end of a frangible line for accessing the pulling end to initiate a tear along the frangible line.

38. The medical device of claim 37 wherein the access point is a relatively thinner section of the device body portion.

39. The medical device of claim 35 further comprising a notch adjacent the pulling end of a frangible line for assisting in propagating a tear along the frangible line.

40. An implantable subcutaneous medical device with a passageway therethrough for accommodating an elongated transcutaneous treatment component that, in use, extends from outside a patient's body, through a skin opening, into and through the medical device positioned at an implantation site, and then to an internal body location, the medical device comprising: a device body portion and one or more frangible lines formed within the device body portion, whereby, at the completion of an extended period in use in a patient's body, the device body portion can be disassembled in situ along the frangible line(s) into device pieces that are sized and/or dimensioned for removal from the implantation site through a skin opening that is smaller than the size of an incision originally needed for implanting the medical device.

41. A medical device according to claim 40, wherein the device further comprises a tissue ingrowth skirt disposed along a wall of the device body portion adjacent the skin opening, which skirt either entirely remains in place under the skin at the implantation site when the device body portion is disassembled and removed, or which skirt is biodegradable and/or bioabsorbable so that the physiology of the patient dissolves and clears the tissue ingrowth skirt.

* * * * *